(12) United States Patent
Harada et al.

(10) Patent No.: US 8,295,438 B2
(45) Date of Patent: Oct. 23, 2012

(54) RADIATION IMAGE CAPTURING SYSTEM

(75) Inventors: Daiki Harada, Minami-ashigara (JP);
Yasunori Ohta, Yokohama (JP);
Naoyuki Nishino, Minami-ashigara (JP);
Naoki Mochizuki, Minami-ashigara (JP); Wataru Ito, Hadano (JP); Yoshiro Kitamura, Yokohama (JP); Eiichi Kito, Minami-ashigara (JP); Akio Sato, Kawasaki (JP)

(73) Assignee: FUJIFILM Corporation, Tokyo (JP)

( * ) Notice: Subject to any disclaimer, the term of this patent is extended or adjusted under 35 U.S.C. 154(b) by 827 days.

(21) Appl. No.: 12/413,186

(22) Filed: Mar. 27, 2009

(65) Prior Publication Data
US 2009/0244352 A1    Oct. 1, 2009

(30) Foreign Application Priority Data

Mar. 28, 2008   (JP) ................................ 2008-086462

(51) Int. Cl.
*H05G 1/70* (2006.01)
(52) U.S. Cl. ......................................... 378/98.2; 378/92

(58) Field of Classification Search ................. 378/98.5, 378/92, 98.2
See application file for complete search history.

(56) References Cited

U.S. PATENT DOCUMENTS

| | | | |
|---|---|---|---|
| 6,431,751 B1* | 8/2002 | Everett et al. ................ | 378/197 |
| 7,197,529 B2 | 3/2007 | Nakagawa et al. | |
| 2002/0131553 A1* | 9/2002 | Tsuchino ..................... | 378/118 |
| 2007/0081624 A1* | 4/2007 | Nabatame ...................... | 378/19 |
| 2007/0253531 A1* | 11/2007 | Okuzawa et al. .............. | 378/62 |
| 2008/0063144 A1* | 3/2008 | Belanger ....................... | 378/92 |

FOREIGN PATENT DOCUMENTS

| | | |
|---|---|---|
| JP | 2000-105297 A | 4/2000 |
| JP | 2002-311524 A | 10/2002 |
| JP | 3494683 B2 | 11/2003 |

* cited by examiner

*Primary Examiner* — Glen Kao
(74) *Attorney, Agent, or Firm* — Sughrue Mion, PLLC

(57) ABSTRACT

A radiation image capturing system includes a plurality of image capturing apparatus for acquiring radiation image information of a subject by controlling radiation sources according to predetermined image capturing conditions, a controller for controlling the image capturing apparatus according to the image capturing conditions set therein, and a plurality of display devices associated respectively with the image capturing apparatus, for displaying radiation image information acquired from the image capturing apparatus.

4 Claims, 6 Drawing Sheets

RADIATION IMAGE CAPTURING SYSTEM

BACKGROUND OF THE INVENTION

1. Field of the Invention

The present invention relates to a radiation image capturing system for capturing the radiation image information of a subject with image capturing apparatus.

2. Description of the Related Art

Some medical organizations such as hospitals incorporate a radiation image capturing system combined with an RIS (Radiology Information System). According to the radiation image capturing system, in order to acquire the desired radiation image information of a patient, the doctor sets patient information including the name, gender, age, etc. of the patient, and image capturing conditions including an image capturing method, a body region to be imaged, an image capturing apparatus to be used, and exposure conditions for determining a radiation dose to be applied to the body region to be imaged. The doctor then supplies these items of information to a console installed in the radiological department. The radiological technician who handles the image capturing apparatus operates the console, and controls the image capturing apparatus to acquire the radiation image information of the patient. After predetermined image processing of the acquired radiation image information is performed, the radiation image information is supplied to a viewer which displays radiation images to be interpreted by the doctor for diagnosis.

For capturing a radiation image of the patient, the radiological technician positions of the body region to be imaged with respect to the image capturing apparatus according to the image capturing conditions, and then turns on an exposure switch of the image capturing apparatus to capture the radiation image. Radiation image information representing the captured radiation image is displayed on the console. The radiological technician confirms the radiation image information displayed on the console, and, if necessary, changes image capturing conditions including the body region to be imaged and exposure conditions, and recaptures radiation image information.

Medical organizations such as hospitals have a plurality of image capturing apparatus in the radiological department thereof, and incorporate a system wherein the respective image capturing apparatus are controlled by respective consoles. According to the related art disclosed in Japanese Laid-Open Patent Publication No. 2002-311524, radiation image information acquired from an image capturing apparatus (radiation image reading apparatus) specified by any console (controller) is sent to the console and processed thereby. Since the processing of radiation image information is distributed to the consoles, even if one of the consoles fails to operate, one of the other normal consoles may be selected to process radiation image information without undue interruptions.

In order for the consoles to be selected interchangeably, the consoles need to have the same processing functions. However, these common processing functions are wasteful if the consoles do not suffer a failure. In addition, the radiological department requires a space for installing those consoles.

To avoid the above drawbacks, it may be proposed to minimize the number of consoles used and to make one of the consoles able to control a plurality of image capturing apparatus.

According to the proposal, however, the console assigned to the plural image capturing apparatus is subject to an increased processing burden, and takes a long period of time until it displays radiation image information acquired from the plural image capturing apparatus. Even though the single console can process radiation image information acquired from the plural image capturing apparatus, it is unable to display a plurality of radiation images simultaneously for confirmation. Consequently, the efficiency of confirmation processing of the radiation image information is lowered.

SUMMARY OF THE INVENTION

It is a general object of the present invention to provide a radiation image capturing system which reduces the processing burden on a controller which controls image capturing apparatus and which allows radiation image information acquired from a plurality of image capturing apparatus to be confirmed efficiently.

It is a main object of the present invention to provide a radiation image capturing system which can save space for the system.

According to the present invention, a radiation image capturing system includes a plurality of image capturing apparatus for acquiring radiation image information of a subject by controlling radiation sources according to predetermined image capturing conditions, a controller for controlling the image capturing apparatus according to the image capturing conditions set therein, and a plurality of display devices associated respectively with the image capturing apparatus, for displaying radiation image information acquired from the image capturing apparatus.

Since the display devices display the respective radiation image information acquired from the image capturing apparatus, the controller is free from an undue burden, and respective radiation images of the radiation image information can be confirmed efficiently on the display devices.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENT

Figure 1:
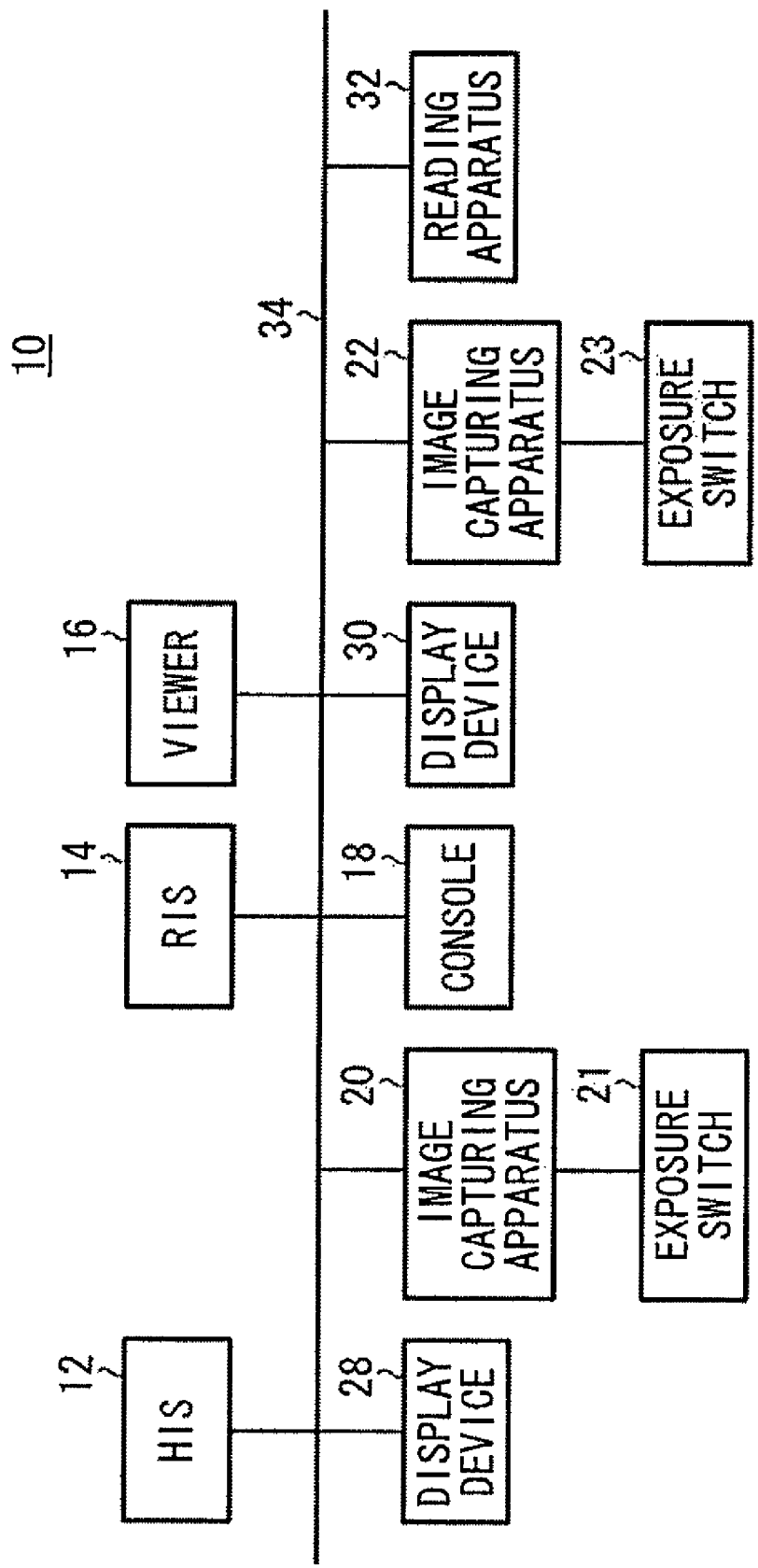
FIG. 1 is a block diagram of a radiation image capturing system according to an embodiment of the present invention.
Figure 2:
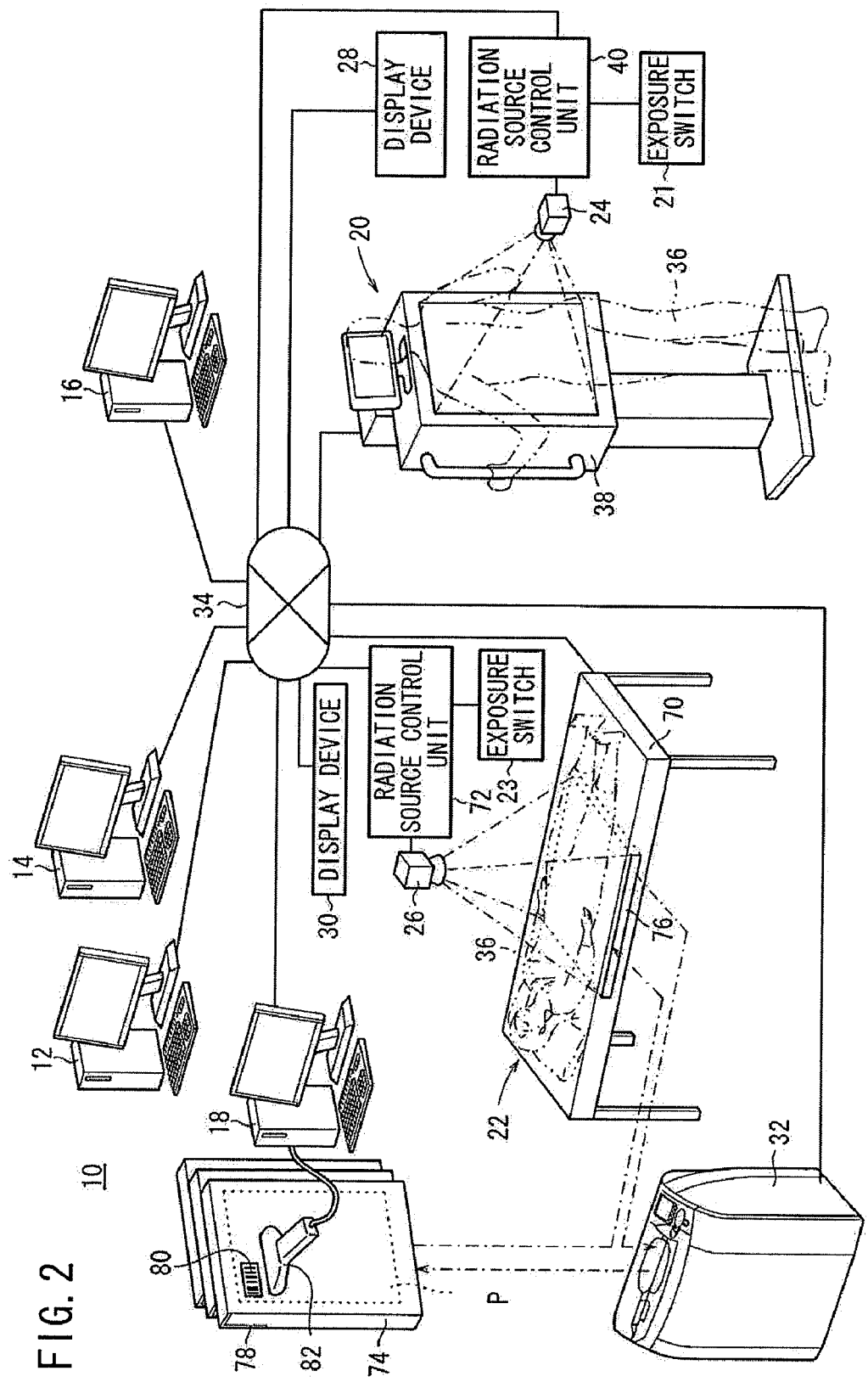
FIG. 2 is a schematic perspective view of the radiation image capturing system shown in FIG. 1.

FIGS. 1 and 2 show a configuration of a radiation image capturing system 10 according to an embodiment of the present invention. As shown in FIGS. 1 and 2, the radiation image capturing system 10 comprises a hospital information system (HIS) 12 for managing medical information in a hospital, a radiology information system (RIS) 14 for managing radiation image capturing processes performed in the radiological department of the hospital under the management of the HIS 12, a viewer 16 for displaying radiation images to be interpreted by the doctor for diagnosis, a console (controller) 18 placed in a control room near image capturing rooms in the radiological department, for centralized management and control of various image capturing apparatus of different specifications, image capturing apparatus 20, 22 placed in respective image capturing rooms, exposure switches 21, 23 for energizing radiation sources 24, 26 of the image capturing apparatus 20, 22 to apply a radiation to a subject, display devices 28, 30 for displaying radiation image information acquired from the image capturing apparatus 20, 22, and a reading apparatus 32 for reading radiation image information which has been recorded in a radiation conversion panel P by the image capturing apparatus 22. The above components of the radiation image capturing system 10 are interconnected by an in-house network 34 in the hospital. If necessary, other consoles, other image capturing apparatus, and components may also be connected to the in-house network 34.

The image capturing apparatus 20 comprises an image capturing base 38 for acquiring radiation image information of a subject 36 which is in an upstanding posture, a radiation source 24, and a radiation source control unit 40 for controlling the radiation source 24 according to an exposure signal from the exposure switch 21. The image capturing base 38 incorporates therein a radiation conversion panel D (see FIG. 3) comprising a solid-state radiation detector for converting a radiation directly into an electric signal.

Figure 3:
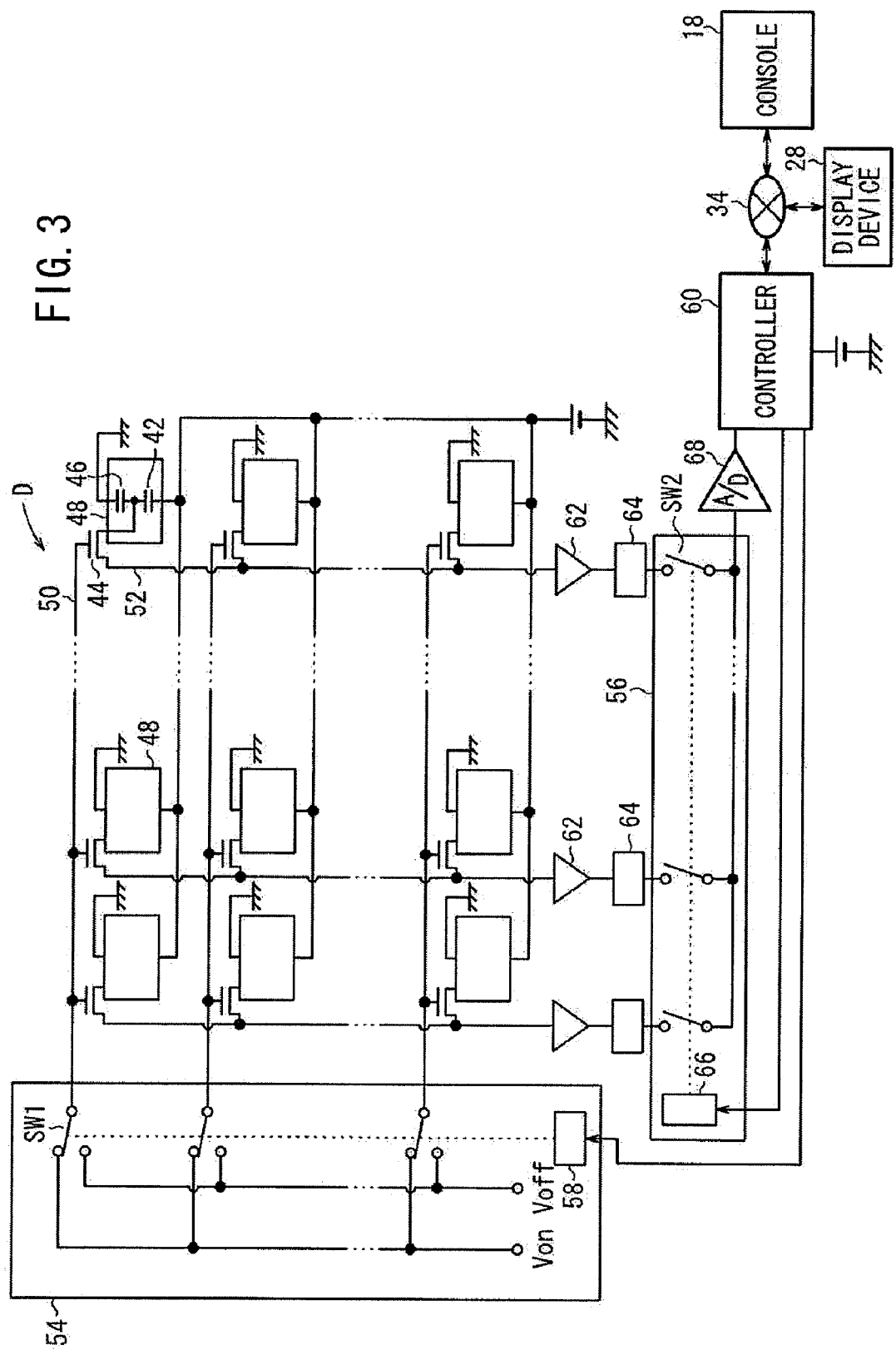
FIG. 3 is a block diagram of a circuit arrangement of a radiation conversion panel used in an image capturing apparatus shown in FIG. 1.

FIG. 3 shows in block form a circuit arrangement of the radiation conversion panel D housed in the image capturing base 38.

The radiation conversion panel D comprises an array of thin-film transistors (TFTS) 44 arranged in rows and columns, a photoelectric conversion layer 42 made of a material such as amorphous selenium (a-Se) for generating electric charges upon detection of a radiation, the photoelectric conversion layer 42 being disposed on the array of TFTS 44, and an array of storage capacitors 46 connected to the photoelectric conversion layer 42. When the radiation is applied to the radiation conversion panel D, the photoelectric conversion layer 42 generates electric charges, and the storage capacitors 46 store the generated electric charges. Then, the TFTs 44 are successively turned on along each row at a time to read the electric charges from the storage capacitors 46 as an image signal. In FIG. 3, the photoelectric conversion layer 42 and one of the storage capacitors 46 are shown as a pixel 48, and the pixel 48 is connected to one of the TFTs 44. Details of the other pixels 48 are omitted from illustration. Since amorphous selenium tends to change its structure and lose its function at high temperatures, it needs to be used in a certain temperature range. Therefore, some means for cooling the radiation conversion panel D should preferably be provided in the image capturing base 38.

The TFTs 44 connected to the respective pixels 48 are connected to respective gate lines 50 extending parallel to the rows and respective signal lines 52 extending parallel to the columns. The gate lines 50 are connected to a line scanning driver 54, and the signal lines 52 are connected to a multiplexer 56 serving as a reading circuit.

The gate lines 50 are supplied with control signals Von, Voff for turning on and off the TFTs 44 along the rows from the line scanning driver 54. The line scanning driver 54 comprises a plurality of switches SW1 for switching between the gate lines 50 and an address decoder 58 for outputting a selection signal for selecting one of the switches SW1 at a time. The address decoder 58 is supplied with an address signal from a controller 60.

The signal lines 52 are supplied with electric charges stored in the storage capacitors 46 of the pixels 48 through the TFTs 44 arranged in the columns. The electric charges supplied to the signal lines 52 are amplified by amplifiers 62 connected respectively to the signal lines 52. The amplifiers 62 are connected through respective sample and hold circuits 64 to the multiplexer 56. The multiplexer 56 comprises a plurality of switches SW2 for successively switching between the signal lines 52 and an address decoder 66 for outputting a selection signal for selecting one of the switches SW2 at a time. The address decoder 66 is supplied with an address signal from the controller 60. The multiplexer 56 has an output terminal connected to an A/D converter 68. A radiation image signal generated by the multiplexer 56 based on the electric charges from the sample and hold circuits 64 is converted by the A/D converter 68 into a digital image signal representing radiation image information, which is supplied to the controller 60. The controller 60 supplies the acquired radiation image information through the in-house network 34 to the console 18.

The TFTs 44, which function as switching elements, may be realized in combination with a CMOS (complementary metal-oxide semiconductor) image sensor or the like, or with other types of imaging devices. Still further, the TFTs 44 may be replaced by CCD (charge-coupled device) sensors, which transmit charges while shifting the charges by means of shift pulses, corresponding to the gate signals within the TFTS.

The image capturing apparatus 22 comprises an image capturing base 70 for acquiring radiation image information of a subject 36 which is in a recumbent posture, a radiation source 26, and a radiation source control unit 72 for controlling the radiation source 26 according to an exposure signal from the exposure switch 23. The image capturing base 70 has a slot 76, defined in a side wall thereof, through which a cassette 74 housing a radiation conversion panel P in the form of a stimulable phosphor panel therein can be loaded into the image capturing base 70.

The radiation conversion panel P comprises a support body and a stimulable phosphor layer disposed on the support body. The stimulable phosphor layer stores the energy of a radiation that is applied thereto. When the stimulable phosphor layer is irradiated with stimulating light, it emits stimulated light depending on the stored energy. When the stimulable phosphor layer is irradiated with erasing light, it discharges any remaining energy stored therein and can be reused.

The radiation conversion panel P housed in the cassette 74 is removable from the cassette 74 when a lid 78 on the cassette 74 is opened. A bar code 80 which records therein identification information including a unique number for identifying the radiation conversion panel P housed in the cassette 74, the size of the radiation conversion panel P, the sensitivity of the radiation conversion panel P, etc. is applied to an outer surface of the cassette 74. The bar code 80 can be read by a bar-code reader 82 connected to the console 18.

The reading apparatus 32 serves to read the radiation image information recorded in the radiation conversion panel P. The reading apparatus 32 is constructed as shown in FIG. 4.

Figure 4:
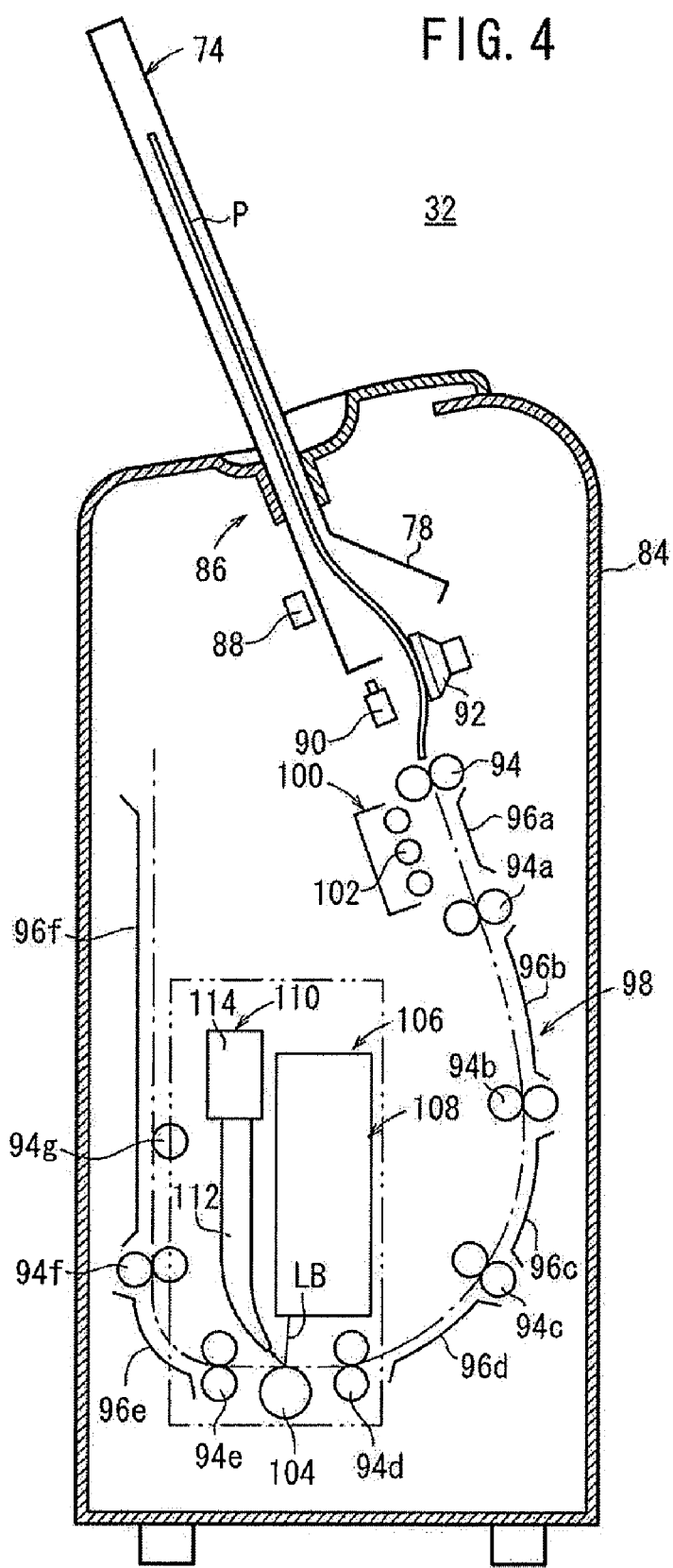
FIG. 4 is a vertical cross-sectional view of a reading apparatus of the radiation image capturing system.

As shown in FIG. 4, the reading apparatus 32 has a cassette loader 86 disposed in an upper portion of a casing 84. The cassette loader 86 is loaded with the cassette 74 which houses therein the radiation conversion panel P with recorded radiation image information. The casing 84 of the reading apparatus 32 accommodates therein, near the cassette loader 86, a bar-code reader 88 for reading the identification information recorded in the bar code 80 on the cassette 74, an unlock mechanism 90 for unlocking the lid 78 of the cassette 74, a suction cup 92 for attracting and removing the radiation conversion panel P from the cassette 74 at the time the lid 78 is opened, and a pair of nip rollers 94 for gripping and feeding the radiation conversion panel P removed by the suction cup 92.

The nip rollers 94 are followed by a plurality of feed rollers 94a through 94g and a plurality of guide plates 96a through 96f which jointly make up a curved feed path 98. The curved feed path 98 extends downwardly from the cassette loader 86, then extends substantially horizontally at its lowermost portion, and then extends substantially vertically upwardly. The curved feed path 98 thus shaped is effective to make the reading apparatus 32 small in size.

Between the nip rollers 94 and the feed rollers 94a, there is disposed an erasing unit 100 for erasing radiation image information remaining in the radiation conversion panel P from which desired radiation image information has been read. The erasing unit 100 has a plurality of erasing light sources 102 such as cold cathode-ray tubes or the like for emitting erasing light.

A platen roller 104 is disposed between the feed rollers 94d, 94e which are positioned in the lowermost portion of the curved feed path 98. The platen roller 104 is disposed beneath a scanning unit 106 for reading the desired radiation image information recorded in the radiation conversion panel P.

The scanning unit 106 comprises a stimulator 108 for emitting a laser beam LB as stimulating light to scan the radiation conversion panel P and a reader 110 for reading stimulated light, which represents the radiation image information, emitted from the radiation conversion panel P which is stimulated by the laser beam LB.

The reader 110 comprises a light guide 112 having a lower end disposed near the radiation conversion panel P over the platen roller 104, and a photomultiplier 114 connected to an upper end of the light guide 112 for converting the stimulated light from the radiation conversion panel P into an electric signal which represents the radiation image information stored in the radiation conversion panel P. The photomultiplier 114 supplies the electric signal representing the radiation image information to the console 18 through the in-house network 34.

Figure 5:
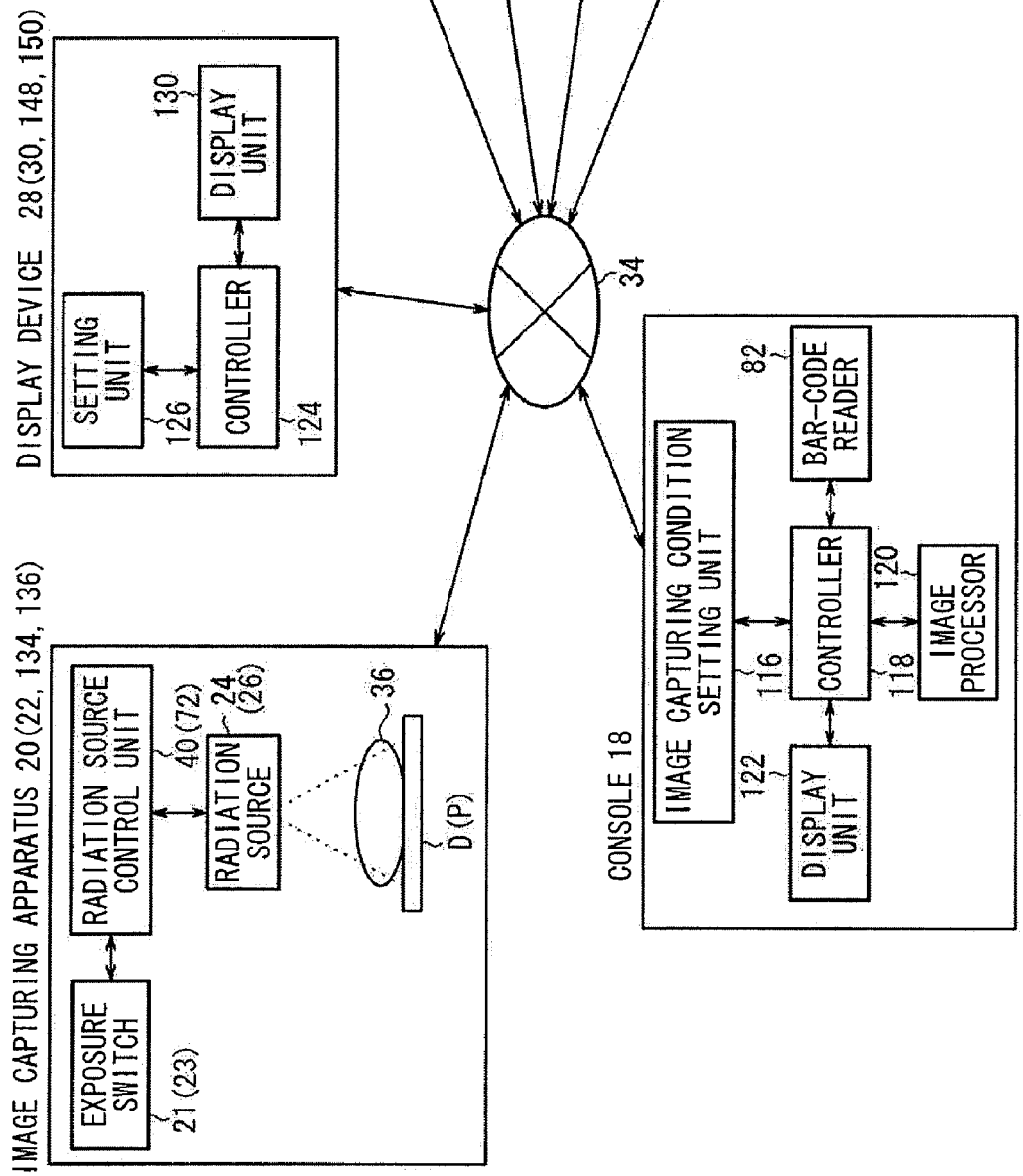
FIG. 5 is a control block diagram of a console, an image capturing apparatus, display devices, and other components of the radiation image capturing system shown in FIG. 1.

FIG. 5 shows a control block diagram of the console 18, the image capturing apparatus 20, 22, the display devices 28, 30, and other components of the radiation image capturing system 10.

The console 18 includes an image capturing condition setting unit 116 for acquiring, through in-house network 34, patient information including the name, gender, age, etc. of the patient, which has been set using the HIS 12, and image capturing conditions including an image capturing method for capturing radiation image information of the patient, a body region to be imaged, an image capturing apparatus to be used, and exposure conditions including a tube voltage, a tube current, a radiation exposure time, etc. to be set in the radiation source of the image capturing apparatus to be used, which have been set by the doctor using the RIS 14, and changing and setting image capturing conditions, a controller 118 for controlling the image capturing apparatus 20, 22, an image processor 120 for processing radiation image information acquired from the image capturing apparatus 20, 22, and a display unit 122 for displaying an image capturing menu including image capturing conditions set by the image capturing condition setting unit 116 and displaying processed radiation image information.

Each of the display devices 28, 30 includes a controller 124, a setting unit 126 for changing and setting image capturing conditions for the radiation source control units 40, 72 of the image capturing apparatus 20, 22, and a display unit 130 for displaying an image capturing menu including image capturing conditions set by the setting unit 126 and also displaying preview images of radiation image information acquired from the image capturing apparatus 20, 22.

Figure 6:
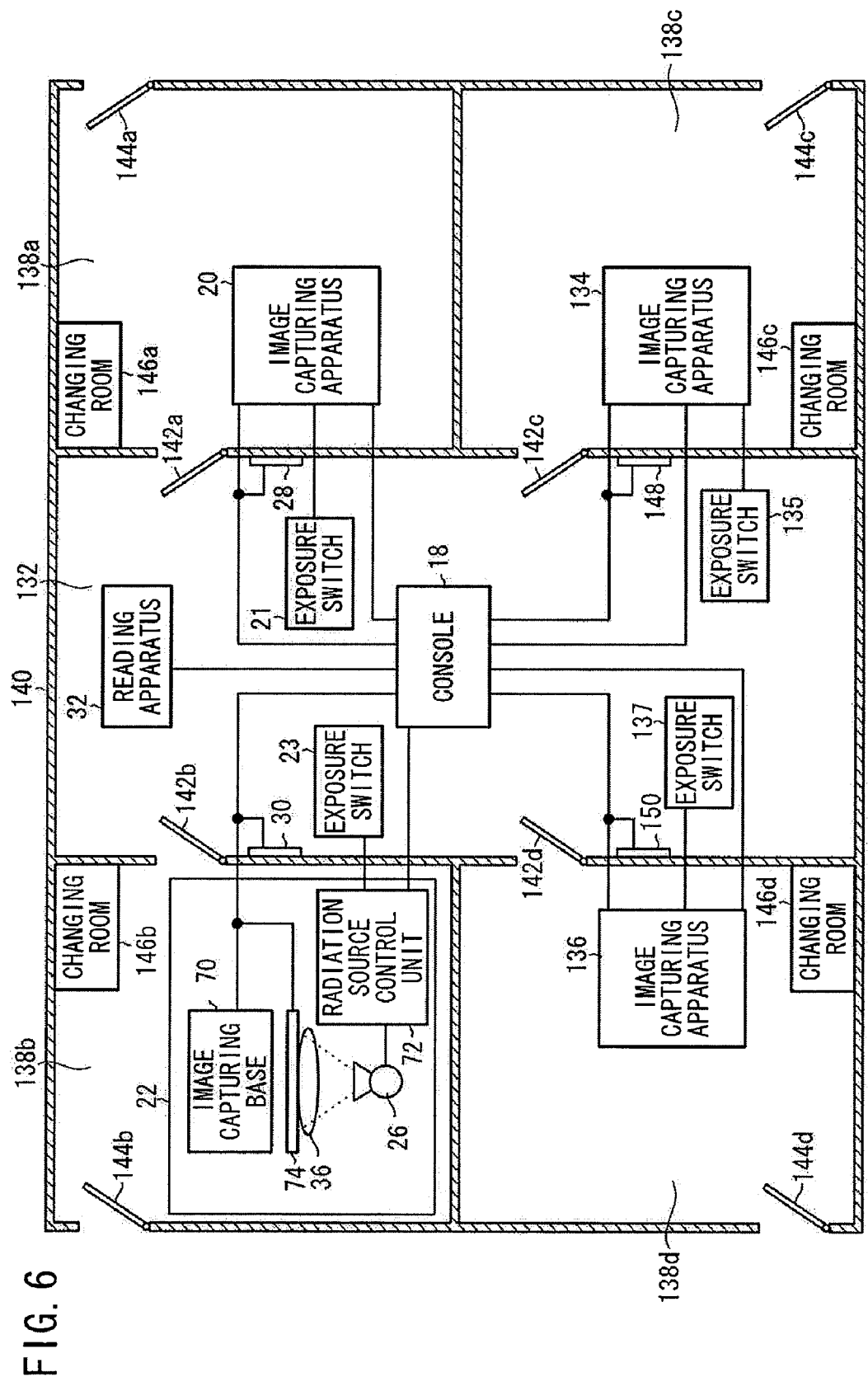
FIG. 6 is a plan view showing the layout of a control room where the console, the display devices, and the reading apparatus are located and image capturing rooms where image capturing apparatus of the radiation image capturing system are located.

FIG. 6 shows an example of the layout of a control room 132 where the console 18, the display devices 28, 30, 148, 150, and the reading apparatus 32 are located, and image capturing rooms 138a through 138d where the image capturing apparatus 20, 22, 134, 136 are located, respectively.

The control room 132 and the image capturing rooms 138a through 138d are isolated by partition walls 140 disposed therebetween which are impermeable to radiations. The radiological technician can move between the control room 132 and the image capturing rooms 138a through 138d through doors 142a, 142b, 142c, 142d that are provided in the partition walls 140 between the control room 132 and the image capturing rooms 138a through 138d. The image capturing rooms 138a through 138d have outer partition walls 140 positioned remotely from the control room 132 and having doors 144a, 144b, 144c, 144d, respectively, through which patients as the subject 36 can move into and out of the image capturing rooms 138a through 138d. Moreover, the respective image capturing rooms 138a through 138d have changing rooms 146a through 146d, in which the patients as the subjects 36 take off and put on clothes. Meanwhile, the control room 132 accommodates therein exposure switches 21, 23, 135, 137 for supplying exposure signals to the respective image capturing apparatus 20, 22, 134, 136 that are placed in the respective image capturing rooms 138a through 138d, and the display devices 28, 30, 148, 150 for displaying radiation image information acquired from the image capturing apparatus 20, 22, 134, 136, respectively.

The display devices 28, 30, 148, 150 comprise flat display panels such as liquid crystal panels, plasma display panels, or the like, and are wall-mounted display devices respectively on the partition walls 140 between the control room 132 and the image capturing rooms 138a through 138d. Therefore, the display devices 28, 30, 148, 150 in the form of flat display panels mounted on the partition walls 140 do not occupy large spaces in the control room 132. Because of the wall-mounted display devices, the technician in the control room 132 can easily confirm the contents displayed on the display devices 28, 30, 148, 150.

The radiation image capturing system 10 according to the present invention is basically constructed as described above. Operation of the radiation image capturing system 10 will be described below.

First, patient information such as the name, gender, age, etc. of a patient is set using the HIS 12. Then, the doctor sets image capturing conditions including an image capturing method for capturing radiation image information of the patient, a body region to be imaged, an image capturing apparatus to be used, and exposure conditions including a tube voltage, a tube current, a radiation exposure time, etc. to be set in the radiation source of the image capturing apparatus to be used, in relation to the patient information, using the RIS 14. The patient information and the image capturing conditions set as image capturing instruction information using the HIS 12 and the RIS 14 are sent via the in-house network 34 to the console 18 installed in the control room 132 of the radiological department. The console 18 displays the sent image capturing instruction information on the display unit 122.

Meanwhile, the radiological technician who has been waiting in the control room 132 confirms the image capturing instruction information displayed on the display unit 122, and, if necessary, changes or sets image capturing conditions using the image capturing condition setting unit 116. For example, if the image capturing apparatus selected by the doctor is being in use or serviced for maintenance, then the radiological technician changes the image capturing apparatus to another image capturing apparatus that may be available, using the image capturing condition setting unit 116. The radiological technician may also change or set image capturing conditions including the tube voltage, tube current, the irradiation time, etc. depending on the body region to be imaged of the subject 36.

Then, the radiological technician starts to capture radiation image information of the subject 36 using the console 18. The radiological technician selects the subject 36 from the image capturing instruction information displayed on the display unit 122 of the console 18, and guides the subject 36 to one of the image capturing rooms 138a through 138d in which the image capturing apparatus based on the image capturing conditions set for the subject 36 is installed. If the image capturing room 138a is selected, for example, the subject 36 is guided into the image capturing room 138a by opening the door 144a, and then changes clothes in a changing room 146a. The radiological technician enters the image capturing room 138a by opening the door 142a, adjusts the position of the image capturing base 38 of the image capturing apparatus 20, adjusts the image capturing posture of the subject 36, and goes from the image capturing room 138a back into the control room 132.

If the image capturing room 138a is selected, the controller 118 of the console 18 sends the image capturing conditions for the selected subject 36 to the radiation source control unit 40 of the image capturing apparatus 20 and the display device 28. Based on the image capturing conditions, the exposure conditions including the tube voltage, the tube current, and the radiation exposure time for the radiation source 24 are set in the radiation source control unit 40. The display unit 130 of the display device 28 displays the name of the patient, the name of the person who captures radiation image information, and the image date and time, and also displays an image capturing menu including the information of the body region to be imaged and the exposure conditions such as the tube voltage, tube current, and the radiation exposure time.

At this time, the radiological technician can change or reset the image capturing conditions using the setting unit 126 of the display device 28. The changed or reset image capturing conditions are sent from the display device 28 to the radiation source control unit 40 of the image capturing apparatus 20 to adjust the radiation source control unit 40. The changed or reset image capturing conditions are also sent via the in-house network 34 to the console 18 which then changes the corresponding image capturing conditions.

The display unit 130 of the display device 28 also displays differences between the standard image capturing conditions set using the RIS 14 and the image capturing conditions that are changed by the radiological technician, e.g., the body thickness of the subject 36, whether the subject 36 is a child or not, and whether the subject 36 is pregnant or not, to allow the radiological technician to objectively judge whether the image capturing conditions that are changed by the radiological technician are suitable or not. If the subject 36 is pregnant, then the display device 28 may display an alarm message or produce an alarm sound to call the radiological technician's attention to the image capturing conditions.

After the radiological technician has confirmed the image capturing conditions displayed on the display unit 130 of the display device 28 or changed the image capturing conditions if necessary, the radiological technician starts to capture radiation image information of the subject 36. When the radiological technician presses the exposure switch 21, it sends an exposure signal through the radiation source control unit 40 to the radiation source 24. In response to the exposure signal, the radiation source 24 outputs a radiation controlled according to the exposure conditions set in the radiation source control unit 40, and applies the radiation to the subject 36.

The radiation that has passed through the subject 36 is applied to the radiation conversion panel D housed in the image capturing base 38, and the radiation image information of the subject 36 is recorded in the radiation conversion panel D.

The radiation is converted into electric signals by the photoelectric conversion layer 42 of the pixels 48 of the radiation conversion panel D (FIG. 3). The electric signals are stored as electric charges in the storage capacitors 46. The stored electric charges, which represent radiation image information of the subject 36, are read from the storage capacitors 46 according to address signals which are supplied from the controller 60 to the line scanning driver 54 and the multiplexer 56.

Specifically, in response to the address signal supplied from the controller 60, the address decoder 58 of the line scanning driver 54 outputs a selection signal to select one of the switches SW1, which supplies the control signal Von to the gates of the TFTs 44 connected to the gate line 50 corresponding to the selected switch SW1. In response to the address signal supplied from the controller 60, the address decoder 66 of the multiplexer 56 outputs a selection signal to successively turn on the switches SW2 to switch between the signal lines 52 for thereby reading the radiation image information representative of the electric charges stored in the storage capacitors 46 of the pixels 48 connected to the selected gate line 50, through the signal lines 52.

The radiation image information read from the storage capacitors 46 of the pixels 48 connected to the selected gate line 50 is amplified by the respective amplifiers 62, sampled by the sample and hold circuits 64, supplied to the A/D converter 68 through the multiplexer 56. The radiation image information converted into the digital signal is transmitted from the controller 60 to the display device 28 through the in-house network 34.

Similarly, the address decoder 58 of the line scanning driver 54 successively turns on the switches SW1 to switch between the gate lines 50 according to the address signal supplied from the controller 60. The radiation image information representative of the electric charges stored in the storage capacitors 46 of the pixels 48 connected to the successively selected gate lines 50 is read out through the signal lines 52, and processed by the multiplexer 56 and the A/D converter 68 into digital signals, which are transmitted from the controller 60 to the display device 28 through the in-house network 34.

The display device 28 displays the received digital signals representative of the radiation image information on the display unit 130 thereof. At this time, the radiological technician can confirm a preview image of the captured radiation image information of the subject 36 on the display unit 130 of the display device 28 which is located adjacent to the exposure switch 21. The preview image may be of such a resolution that the radiological technician can barely confirm the image capturing conditions.

At the time of confirming the preview image, if the radiological technician judges that the captured radiation image information is inappropriate, then the radiological technician changes image capturing conditions using the setting unit 126 of the display device 28 or the image capturing condition setting unit 116 of the console 18. If the image capturing posture or the body region to be imaged of the subject 36 does not need to be changed, then the radiological technician can immediately recapture radiation image information of the subject 36 by pressing the exposure switch 21, without troubling the subject 36. The recaptured radiation image information may be displayed on the display unit 130 of the display device 28 for the radiological technician to confirm again.

When the recaptured radiation image information is displayed on the display unit 130, the previously captured radiation image information and the image capturing conditions therefor may simultaneously be displayed on the display unit 130. In this manner, the radiological technician can more accurately determine whether the recaptured radiation image information based on the changed image capturing conditions is appropriate or not.

If the captured radiation image information is appropriate, then the captured radiation image information is sent from the image capturing apparatus 20 or the display device 28 to the console 18. In the console 18, the captured radiation image information is processed by the image processor 120 and then sent to the viewer 16 via the in-house network 34. The doctor then interprets for diagnosis a radiation image that is displayed by the viewer 16 based on the radiation image information.

If the image capturing room 138b is selected, then the display unit 130 of the display device 30 that is connected to the image capturing apparatus 22 installed in the image capturing room 138b displays the image capturing conditions for the selected subject 36, as with the display device 28. The radiological technician can change or reset the image capturing conditions on the display device 30. The image capturing conditions are sent from the display device 30 to the radiation source control unit 72 of the image capturing apparatus 22 where the image capturing conditions are set in the radiation source control unit 72.

The radiological technician uses the bar-code reader 82 connected to the console 18 to read the bar code 80 applied to the cassette 74, thereby acquiring identification information including a unique number for identifying the radiation conversion panel P housed in the cassette 74, the size of the radiation conversion panel P, the sensitivity of the radiation conversion panel P, etc.

After having loaded the cassette 74 into the slot 76 of the image capturing apparatus 22, the radiological technician presses the exposure switch 23. The radiation source 26 outputs and applies the radiation to the subject 36.

The radiation that has passed through the subject 36 is applied to the radiation conversion panel P housed in the cassette 74. As a result, radiation image information of the subject 36 is recorded in the radiation conversion panel P.

The radiological technician then removes the cassette 74 housing therein the radiation conversion panel P with the recorded radiation image information from the image capturing apparatus 22, and thereafter loads the cassette 74 into the cassette loader 86 of the reading apparatus 32. When the cassette 74 is loaded into the cassette loader 86, the bar-code reader 88 in the cassette loader 86 reads the bar code 80 applied to the cassette 74 to acquire the identification information including the unique number, the size, the sensitivity, etc. of the radiation conversion panel P. The acquired identification information is compared with the identification information read by the bar-code reader 82 connected to the console 18 to confirm the correspondence between the subject 36 and the radiation image information.

After the identification information is read, the unlock mechanism 90 is actuated to unlock and open the lid 78. The suction cup 92 attracts the radiation conversion panel P, removes the radiation conversion panel P out of the cassette 74, and feeds the radiation conversion panel P between the nip rollers 94. The radiation conversion panel P which is gripped by the nip rollers 94 is then fed through the curved feed path 98 made up of the feed rollers 94a through 94g and the guide plates 96a through 96f to a position beneath the scanning unit 106.

Beneath the scanning unit 106, the radiation conversion panel P is fed substantially horizontally in an auxiliary scanning direction by the feed rollers 94d, 94e. At the same time, the laser beam LB output from the stimulator 108 is guided to the radiation conversion panel P, thereby scanning the radiation conversion panel P in a main scanning direction that is perpendicular to the auxiliary scanning direction.

By being irradiated with the laser beam LB, the radiation conversion panel P is stimulated to emit stimulated light representative of the radiation image information recorded therein. The stimulated light is applied to the lower end of the light guide 112 which is disposed near the radiation conversion panel P and extends in the main scanning direction. The stimulated light which has entered the light guide 112 is repeatedly reflected in the light guide 112 and guided to the photomultiplier 114. The photomultiplier 114 converts the stimulated light into an electric signal representative of the radiation image information recorded in the radiation conversion panel P. In this manner, the radiation image information recorded in the radiation conversion panel P is read out by the scanning unit 106 of the reading apparatus 32.

The radiation image information thus read out by the scanning unit 106 is transmitted to the display device 30 through the in-house network 34. The display device 30 displays a preview image of the received radiation image information on the display unit 130 as with the display device 28. The radiological technician confirms the preview image and, if necessary, may change image capturing conditions and then immediately recapture radiation image information of the subject 36.

If the captured radiation image information is appropriate, then the captured radiation image information is sent from the image capturing apparatus 22 or the display device 30 to the console 18. In the console 18, the captured radiation image information is processed by the image processor 120 and then sent to the viewer 16 via the in-house network 34. The doctor then interprets for diagnosis a radiation image that is displayed by the viewer 16 based on the radiation image information.

According to the embodiment of the present invention, the single console 18 shared by the image capturing apparatus 20, 22, 134, 136 serves as a space saver in the control room 132. Before radiation image information acquired from the image capturing apparatus 20, 22, 134, 136 in the respective image capturing rooms 138a through 138d is processed by the console 18, the radiation image information is displayed on the display devices 28, 30, 148, 150 independent of the console 18 for the radiological technician to confirm individually.

Even if radiation image information acquired from the image capturing apparatus 20, 22, 134, 136 in the image capturing rooms 138a through 138d is acquired substantially simultaneously, the console 18 is free from an undue burden, and the radiological technician can confirm preview images of the radiation image information on the individual display devices 28, 30, 148, 150.

Although a certain preferred embodiment of the present invention has been shown and described in detail, it should be understood that various changes and modifications may be made to the embodiment without departing from the scope of the invention has set forth in the appended claims.

For example, the aforementioned radiation conversion panel D makes up a direct conversion type of radiation detection device, which converts the radiation dose of the irradiated radiation directly into electric signals through the photoelectric conversion layer 42. However, in place of this structure, an indirect conversion type of radiation detection device in which irradiated radiation is converted initially into visible light by a scintillator, and thereafter, the visible light is converted into electric signals using a solid-state detector element formed from amorphous silicon (a-Si) or the like, may also be used (see, Japanese Patent No. 3494683).

Further, the radiation image information can be obtained using a light readout type of radiation detection device. With such a light readout type of radiation detection device, radiation is irradiated onto respective solid state detection elements arranged in a matrix form, and an electrostatic latent image corresponding to the irradiation dose is stored cumulatively in the solid state detection elements. When the electrostatic latent image is read out, reading light is irradiated onto the radiation detection device, and the generated current values are acquired as radiation image information. Further, by irradiating the radiation detection device with erasing light, the radiation image information in the form of a residual electrostatic latent image can be erased and the radiation detection device can be reused (see, Japanese Laid-Open Patent Publication No. 2000-105297).

Furthermore, in the present embodiment, a case has been described in which patient information is set in the HIS 12 by a doctor, image capturing instruction information is set in the RIS 14 by a doctor or a technician, and such information is supplied to the console 18 over the in-house network 34. However, in place of this configuration, the patient information and image capturing instruction information may also be set directly in the console 18, or alternatively, the patient information and image capturing instruction information may be set either by the HIS 12 or the RIS 14.

What is claimed is:

1. A radiation image capturing system comprising:
   a plurality of image capturing apparatus for acquiring radiation image information of a subject by controlling radiation sources according to predetermined image capturing conditions;
   a controller for controlling the image capturing apparatus according to the image capturing conditions set therein; and
   a plurality of display devices associated respectively with the image capturing apparatus, for displaying radiation image information acquired from the image capturing apparatus,
   wherein the plurality of image capturing apparatus are installed in a plurality of image capturing rooms, and
   the controller and the plurality of display devices are disposed in a control room.

2. A radiation image capturing system according to claim 1, wherein the controller processes the radiation image information acquired from the image capturing apparatus.

3. A radiation image capturing system according to claim 1, wherein the display devices display the image capturing conditions set in the image capturing apparatus.

4. A radiation image capturing system according to claim 1,
   wherein the display devices are mounted respectively on partition walls isolating the control room from the image capturing rooms.

\* \* \* \* \*